(12) United States Patent
Kim et al.

(10) Patent No.: US 10,053,698 B2
(45) Date of Patent: Aug. 21, 2018

(54) **RECOMBINANT MICROORGANISMS OF *ESCHERICHIA* WITH L-THREONINE PRODUCTIVITY AND METHOD OF PRODUCING L-THREONINE USING THE SAME**

(71) Applicant: CJ Cheiljedang Corporation, Seoul (KR)

(72) Inventors: Hyung Joon Kim, Seoul (KR); Su Yon Kwon, Gyeonggi-do (KR); Eun Sung Koh, Gyeonggi-do (KR); Ji Sun Lee, Gyeonggi-do (KR); Keun Cheol Lee, Gyeonggi-do (KR); Young Bin Hwang, Seoul (KR); Hyeong Pyo Hong, Gangwon-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/112,992

(22) PCT Filed: Apr. 25, 2014

(86) PCT No.: PCT/KR2014/003649
§ 371 (c)(1),
(2) Date: Jul. 20, 2016

(87) PCT Pub. No.: WO2015/122569
PCT Pub. Date: Aug. 20, 2015

(65) Prior Publication Data
US 2017/0002365 A1 Jan. 5, 2017

(30) Foreign Application Priority Data

Feb. 12, 2014 (WO) ................ PCT/KR2014/001154

(51) Int. Cl.
*C12N 1/20* (2006.01)
*C12P 13/08* (2006.01)
(Continued)

(52) U.S. Cl.
CPC .............. *C12N 15/70* (2013.01); *C07K 14/34* (2013.01); *C12N 1/20* (2013.01); *C12P 13/08* (2013.01)

(58) Field of Classification Search
None
See application file for complete search history.

(56) References Cited

U.S. PATENT DOCUMENTS 7,332,310 B2 2/2008 Nakagawa et al.
2006/0030009 A1* 2/2006 Livshits ............... C12N 9/1205
435/106

(Continued)

FOREIGN PATENT DOCUMENTS

KR 10-1058894 B1 8/2011
KR 10-1145943 B1 5/2012

(Continued)

OTHER PUBLICATIONS

Venter et al., "Molecular dissection of membrane-transport proteins: mass spectrometry and sequence determination of the galactose-H+ symport protein, GalP, of *Escherichia coli* and quantitative assay of the incorporation of [ring-2-13C]histidine and 15NH3", Biochemical Journal, vol. 363, pp. 243-252, 2002.*

(Continued)

*Primary Examiner* — Richard C Ekstrom
(74) *Attorney, Agent, or Firm* — Swanson & Bratschun, L.L.C.

(57) ABSTRACT

The present invention relates to an *E. coli* mutant strain having enhanced L-threonine productivity, which is obtained by introducing the permease of *Corynebacterium*

(Continued)

origin, and to method of producing L-threonine using the *E. coli* mutant strain.

6 Claims, 4 Drawing Sheets

(51) Int. Cl.
    *C12N 15/70*     (2006.01)
    *C07K 14/34*     (2006.01)

(56) References Cited

U.S. PATENT DOCUMENTS

| | | | |
|---|---|---|---|
| 2006/0088919 A1* | 4/2006 | Rybak | C12P 13/04 435/108 |
| 2006/0257979 A1 | 11/2006 | Dusch | |
| 2007/0118916 A1* | 5/2007 | Puzio | C12N 15/8214 800/278 |
| 2009/0275090 A1* | 11/2009 | Ueda | C12P 13/04 435/110 |
| 2009/0275091 A1* | 11/2009 | Ueda | C12P 13/04 435/110 |
| 2011/0111466 A1* | 5/2011 | Ju | C12N 9/1205 435/108 |
| 2011/0244528 A1* | 10/2011 | Ikeda | C07K 14/34 435/106 |
| 2011/0269183 A1* | 11/2011 | Lee | C12N 1/20 435/69.1 |
| 2012/0122163 A1* | 5/2012 | Ju | C07K 14/26 435/115 |
| 2012/0252078 A1* | 10/2012 | Ju | C12P 13/04 435/115 |

FOREIGN PATENT DOCUMENTS

WO     WO 2004/087937 A1     10/2004
WO     WO 2007/119576 A1     10/2007

OTHER PUBLICATIONS

Ikeda et al., "Identification and application of a different glucose uptake system that functions as an alternative to the phosphotransferase system in *Corynebacterium glutamicum*", Applied Microbiology and Biotechnology, vol. 90, pp. 1443-1451, 2011.*
Dong et al., "Metabolic engineering of *Escherichia coli* and *Corynebacterium glutamicum* for the production of L-threonine", Biotechnology Adv. Aug. 3, 2010, vol. 29(1): 11-23; doi:10.1016/j.biotechadv.2010.07.009.
GenBank Accession No. WP_011013450 https://www.ncbi.nlm.nih.gov, May 24, 2013.
GenBank Accession No. WP_011015598 https://www.ncbi.nlm.nih.gov, May 15, 2013.
International Search Report from PCT/KR2014/001154 dated Jun. 25, 2014.
International Search Report from PCT/KR2014/003649 dated Nov. 26, 2014.
Linder et al., Applied and Environmental Microbiology, 2011, vol. 77, No. 11, pp. 3571-3581, "Phosphotransferase System-Independent Glucose Utilization in *Corynebacterium glutamicum* by Inositol Permeases and Glucokinases".
Bäumchen et al. (2009) FEMS Microbiology Letter 290(2):227-235 "Myo-inositol facilitators Io1T1 and Io1T2 enchance D-mannitol formation from D-fructose in *Corunebacterium glutamicum*".
Extended European Search Report for application No. 14882402.2 dated Oct. 2, 2017.
Linder et al. (2011) Bioengineered Bugs 2(5):291-295 "Impact of a new glucose utilization pathway in amino acid-producing *Corynebactrium glutamicum*".

* cited by examiner

[Fig. 1]

[Fig. 2]
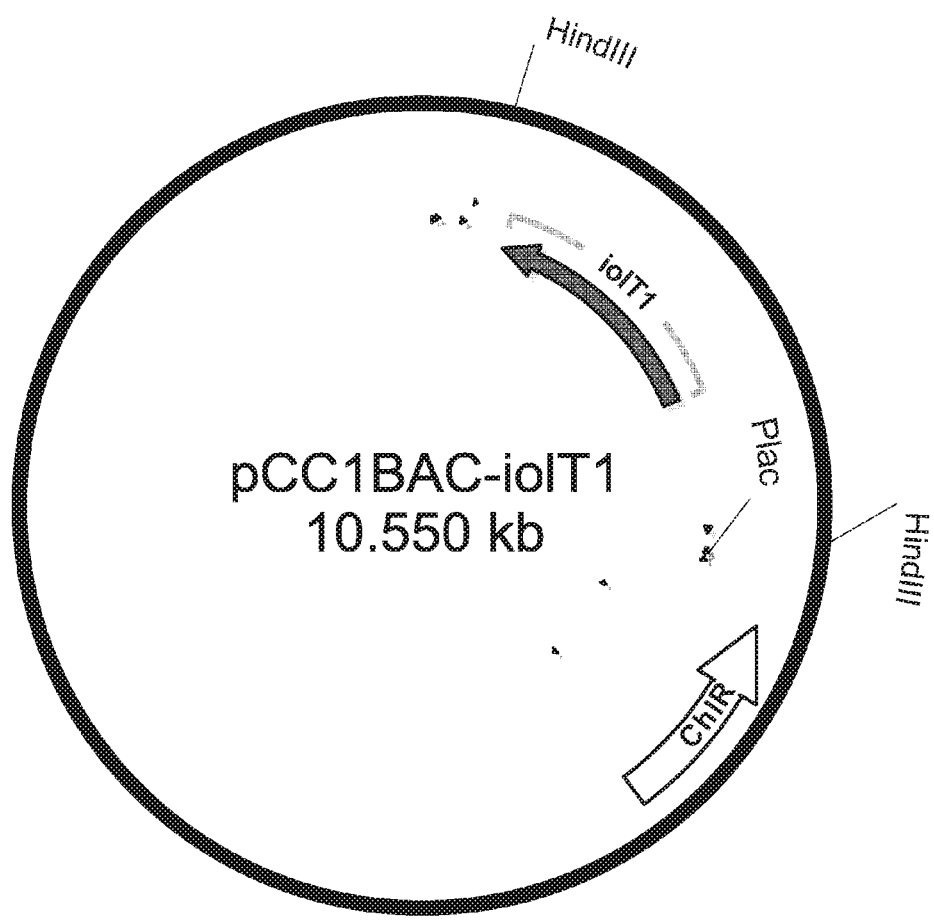

[Fig. 3]
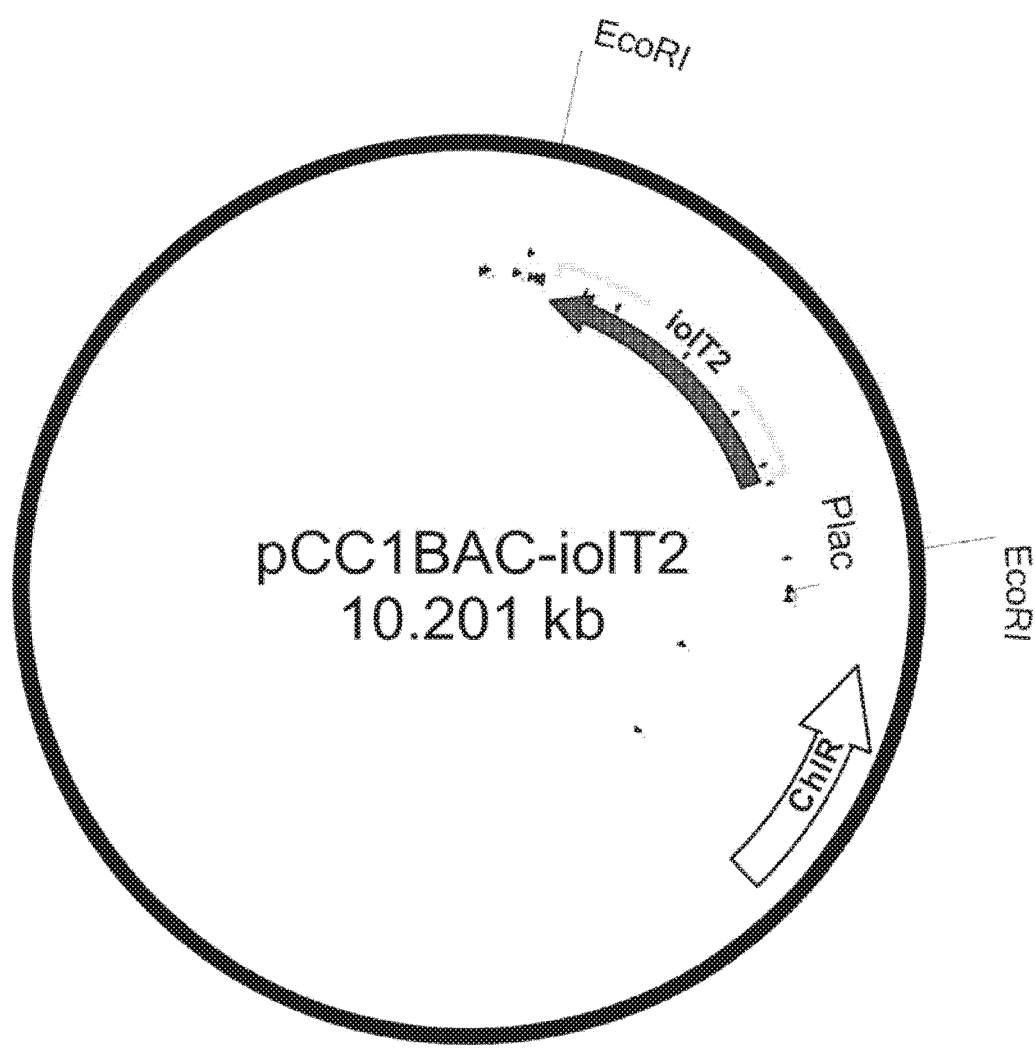

[Fig. 4]
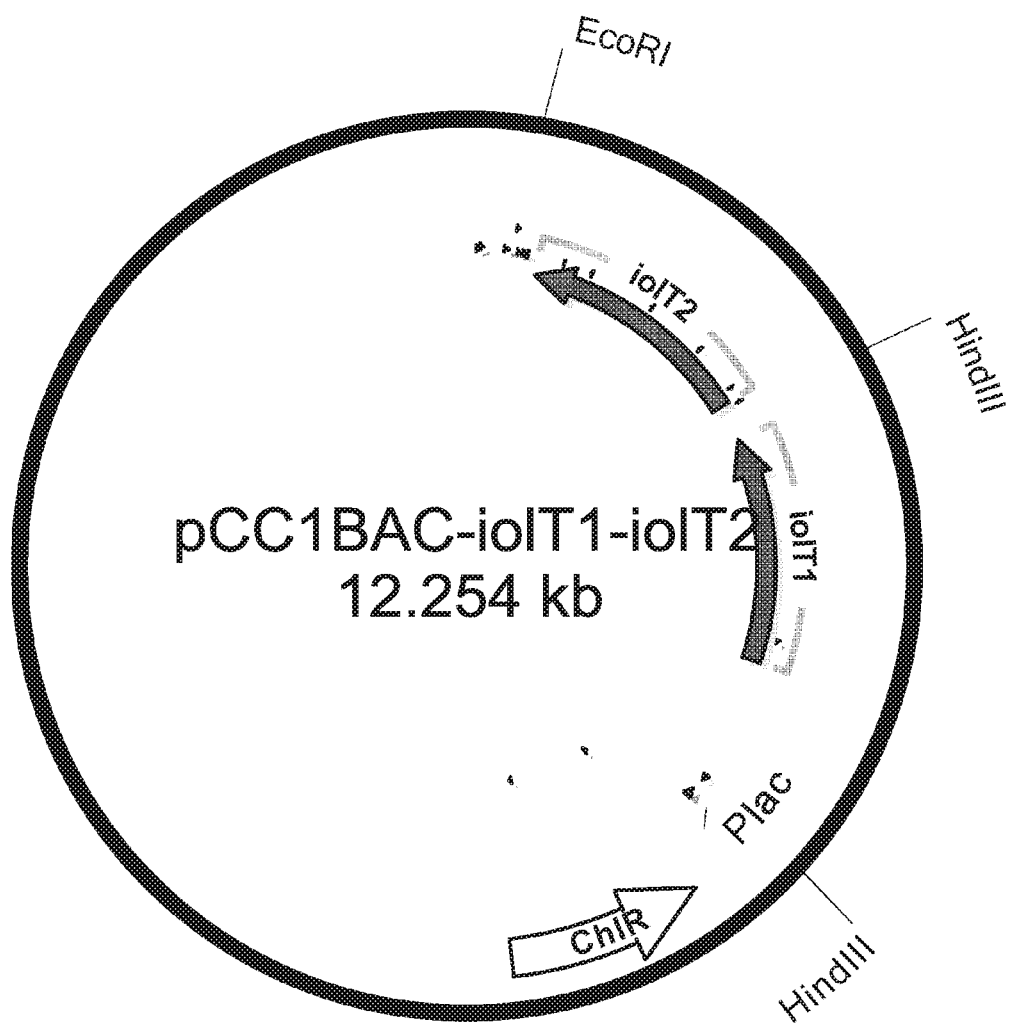

SEQUENCE LISTING

<160> NUMBER OF SEQ ID NOS: 14

<210> SEQ ID NO 1
<211> LENGTH: 491
<212> TYPE: PRT
<213> ORGANISM: Corynebacterium glutamicum

<400> SEQUENCE: 1

Met Ala Ser Thr Phe Ile Gln Ala Asp Ser Pro Glu Lys Ser Lys Lys
1               5                   10                  15

Leu Pro Pro Leu Thr Glu Gly Pro Tyr Arg Lys Arg Leu Phe Tyr Val
            20                  25                  30

Ala Leu Val Ala Thr Phe Gly Gly Leu Leu Phe Gly Tyr Asp Thr Gly
        35                  40                  45

Val Ile Asn Gly Ala Leu Asn Pro Met Thr Arg Glu Leu Gly Leu Thr

-continued

```
                50                  55                  60
Ala Phe Thr Glu Gly Val Val Thr Ser Ser Leu Leu Phe Gly Ala Ala
 65                  70                  75                  80

Ala Gly Ala Met Phe Phe Gly Arg Ile Ser Asp Asn Trp Gly Arg Arg
                 85                  90                  95

Lys Thr Ile Ile Ser Leu Ala Val Ala Phe Phe Val Gly Thr Met Ile
                100                 105                 110

Cys Val Phe Ala Pro Ser Phe Ala Val Met Val Val Gly Arg Val Leu
                115                 120                 125

Leu Gly Leu Ala Val Gly Gly Ala Ser Thr Val Val Pro Val Tyr Leu
            130                 135                 140

Ala Glu Leu Ala Pro Phe Glu Ile Arg Gly Ser Leu Ala Gly Arg Asn
145                 150                 155                 160

Glu Leu Met Ile Val Gly Gln Leu Ala Ala Phe Val Ile Asn Ala
                165                 170                 175

Ile Ile Gly Asn Val Phe Gly His His Asp Gly Val Trp Arg Tyr Met
            180                 185                 190

Leu Ala Ile Ala Ala Ile Pro Ala Ile Ala Leu Phe Phe Gly Met Leu
            195                 200                 205

Arg Val Pro Glu Ser Pro Arg Trp Leu Val Glu Arg Gly Arg Ile Asp
210                 215                 220

Glu Ala Arg Ala Val Leu Glu Thr Ile Arg Pro Leu Glu Arg Ala His
225                 230                 235                 240

Ala Glu Val Ala Asp Val Glu His Leu Ala Arg Glu His Ala Val
            245                 250                 255

Ser Glu Lys Ser Met Gly Leu Arg Glu Ile Leu Ser Ser Lys Trp Leu
            260                 265                 270

Val Arg Ile Leu Leu Val Gly Ile Gly Leu Gly Val Ala Gln Gln Leu
            275                 280                 285

Thr Gly Ile Asn Ser Ile Met Tyr Tyr Gly Gln Val Val Leu Ile Glu
            290                 295                 300

Ala Gly Phe Ser Glu Asn Ala Ala Leu Ile Ala Asn Val Ala Pro Gly
305                 310                 315                 320

Val Ile Ala Val Val Gly Ala Phe Ile Ala Leu Trp Met Met Asp Arg
                325                 330                 335

Ile Asn Arg Arg Thr Thr Leu Ile Thr Gly Tyr Ser Leu Thr Thr Ile
            340                 345                 350

Ser His Val Leu Ile Gly Ile Ala Ser Val Ala Phe Pro Val Gly Asp
            355                 360                 365

Pro Leu Arg Pro Tyr Val Ile Leu Thr Leu Val Val Phe Val Gly
            370                 375                 380

Ser Met Gln Thr Phe Leu Asn Val Ala Thr Trp Val Met Leu Ser Glu
385                 390                 395                 400

Leu Phe Pro Leu Ala Met Arg Gly Phe Ala Ile Gly Ile Ser Val Phe
            405                 410                 415

Phe Leu Trp Ile Ala Asn Ala Phe Leu Gly Leu Phe Phe Pro Thr Ile
            420                 425                 430

Met Glu Ala Val Gly Leu Thr Gly Thr Phe Phe Met Phe Ala Gly Ile
            435                 440                 445

Gly Val Val Ala Leu Ile Phe Ile Tyr Thr Gln Val Pro Glu Thr Arg
            450                 455                 460

Gly Arg Thr Leu Glu Glu Ile Asp Glu Asp Val Thr Ser Gly Val Ile
465                 470                 475                 480
```

Phe Asn Lys Asp Ile Arg Lys Gly Lys Val His
            485                 490

<210> SEQ ID NO 2
<211> LENGTH: 508
<212> TYPE: PRT
<213> ORGANISM: Corynebacterium glutamicum

<400> SEQUENCE: 2

Met Thr Asp Ile Lys Ala Thr Ser Ser Thr Ser Ala Thr Thr Ala Pro
1               5                   10                  15

Thr Ala Gly Arg Pro Ala Arg Arg Leu Gly Gln Ile Ser Leu Val Ala
            20                  25                  30

Cys Leu Gly Gly Leu Leu Phe Gly Tyr Asp Thr Gly Val Ala Asn Gly
        35                  40                  45

Ala Glu Gly His Met Ala Gln Glu Leu Gly Leu Asn Val Leu Gln Leu
    50                  55                  60

Gly Val Val Ile Ser Ser Leu Val Phe Ala Ala Phe Gly Ala Leu
65                  70                  75                  80

Phe Ala Gly Arg Ile Ser Asp Glu Ile Gly Arg Arg Lys Ala Ile Ile
                85                  90                  95

Thr Leu Ser Val Leu Phe Phe Leu Gly Ser Ile Leu Val Val Phe Ser
            100                 105                 110

Pro Ala Gly Glu Leu Gly Gln Phe Tyr Gly Pro Gly Phe Ala Thr Leu
        115                 120                 125

Val Thr Gly Arg Ile Met Leu Gly Leu Ala Val Gly Gly Ala Ser Thr
    130                 135                 140

Val Val Pro Val Tyr Leu Ala Glu Leu Ala Pro Leu Glu Ile Arg Gly
145                 150                 155                 160

Ser Leu Thr Gly Arg Asn Glu Leu Ala Ile Val Thr Gly Gln Leu Leu
                165                 170                 175

Ala Phe Val Ile Asn Ala Leu Ile Ala Val Thr Leu His Gly Val Ile
            180                 185                 190

Asp Gly Ile Trp Arg Ile Met Phe Ala Val Cys Ala Leu Pro Ala Val
        195                 200                 205

Ala Leu Phe Leu Gly Met Leu Arg Met Pro Glu Ser Pro Arg Trp Leu
    210                 215                 220

Val Asn Gln Gly Arg Tyr Asp Asp Ala Arg Arg Val Met Glu Thr Val
225                 230                 235                 240

Arg Thr Pro Glu Arg Ala Lys Ala Glu Met Asp Glu Ile Ile Ala Val
                245                 250                 255

His Ser Glu Asn Asn Ala Ala Leu Pro Gly Val Lys Gln Ser Ser Gly
            260                 265                 270

Gln Ala Ser Gly Gln Val Ser Ser Lys His Thr His Met Ser Ile Gly
        275                 280                 285

Glu Val Leu Ser Asn Lys Trp Leu Val Arg Leu Leu Ile Ala Gly Ile
    290                 295                 300

Gly Val Ala Val Ala Gln Gln Leu Thr Gly Ile Asn Ala Ile Met Tyr
305                 310                 315                 320

Tyr Gly Thr Arg Val Leu Glu Glu Ser Gly Met Ser Ala Glu Met Ala
                325                 330                 335

Val Val Ala Asn Ile Ala Phe Gly Ala Val Ala Val Ile Gly Gly Leu
            340                 345                 350

Ile Ala Leu Arg Asn Met Asp Arg Leu Asp Arg Arg Thr Thr Phe Ile

```
                    355                 360                 365
Ile Gly Leu Ser Leu Thr Thr Thr Phe His Leu Leu Ile Ala Ala Ala
        370                 375                 380
Gly Thr Leu Leu Pro Glu Gly Asn Ser Ile Arg Pro Phe Ala Ile Met
385                 390                 395                 400
Ile Leu Val Val Gly Phe Val Leu Ser Met Gln Thr Phe Leu Asn Val
                405                 410                 415
Ala Val Trp Val Trp Leu Ala Glu Ile Phe Pro Val Arg Met Lys Gly
            420                 425                 430
Ile Gly Thr Gly Ile Ser Val Phe Cys Gly Trp Gly Ile Asn Gly Val
        435                 440                 445
Leu Ala Leu Phe Phe Pro Ala Leu Val Ser Gly Val Gly Ile Thr Phe
    450                 455                 460
Ser Phe Leu Ile Phe Ala Val Val Gly Val Ile Ala Leu Ala Phe Val
465                 470                 475                 480
Thr Lys Phe Val Pro Glu Thr Arg Gly Arg Ser Leu Glu Glu Leu Asp
                485                 490                 495
His Ala Ala Phe Thr Gly Gln Ile Phe Lys Lys Ala
            500                 505

<210> SEQ ID NO 3
<211> LENGTH: 1476
<212> TYPE: DNA
<213> ORGANISM: Corynebacterium glutamicum

<400> SEQUENCE: 3
atggctagta ccttcattca ggccgacagc cctgaaaaaa gtaagaagct gcccccactc      60
acagaaggtc cgtatagaaa gcggctattc tacgttgcac tagttgcgac gtttggtggg     120
ctgctcttcg atatgacac cggagtaatc aacggtgcac tcaacccaat gacacgtgag     180
ctcggactaa ccgcgttcac cgagggtgtt gtaacttctt ccctgctgtt tggtgcagca     240
gctggtgcga tgttttcgg tcgcatttcc gacaactggg gtcgccggaa acaatcatc      300 tcacttgcag tagcttcttt tgtcggcacc atgatctgcg tgtttgctcc atcttttgca     360
gtaatggttg tcggacgtgt gcttcttgga ctcgcagttg gtggcgcttc cactgttgtc     420
cctgtctacc tggctgaact tgctcctttt gaaatccgtg gctcactggc tggccgtaat     480
gagttgatga ttgttgttgg tcagctcgca gcttttgtca tcaatgcgat tattggaaat     540
gttttttgga ccacgatgg tgtgtggcgc tacatgctgg caattgccgc aatcccagca     600
attgccctct tctttggaat gctccgagtt ccagaatccc cacgctggct tgttgagcga     660
ggacgcattg atgaggctcg cgcagttctt gaaaccattc gccctctaga acgtgcccat     720
gcagaagttg ctgatgttga acacctagca agagaagagc acgccgtttc cgagaagtcc     780
atgggcttaa gggaaatttt gtccagcaag tggcttgtgc catcctcct ggtaggtatc     840 ggattgggtg tcgcacagca gctgaccggc atcaactcca tcatgtacta cggccaggtt     900
gttctcattg aggctggttt ctccgagaat gcagctctga tcgccaacgt ggcgccagga     960
gtgatcgcag ttgtcggtgc attcatcgca ctgtggatga tggatcgtat caaccgccgt    1020
accaccctca ttaccggtta ttctctcacc accattagcc acgtattgat cggtatcgca    1080
tccgtagcat tcccagtcgg cgatcctctt cgcccctacg ttatcttgac tctggttgtg    1140
gtcttcgtgg gatccatgca gaccttcctc aactgtagcta cctgggttat gctctctgag    1200
ctcttcccgc tggcaatgcg cggtttcgca atcggtatct cagtgttctt cctctggatc    1260
```

```
gcaaacgcgt tcctcggatt gttcttccca accatcatgg aagcagtagg actaaccgga    1320
accttcttca tgttcgccgg aatcggtgtg gttgccttga tcttcatcta cacccaggtt    1380
cctgaaactc gtggacgtac cttggaggag attgatgagg atgttacttc cggtgtcatt    1440
ttcaacaagg acatccgaaa aggaaaggtg cactaa                              1476

<210> SEQ ID NO 4
<211> LENGTH: 1527
<212> TYPE: DNA
<213> ORGANISM: Corynebacterium glutamicum

<400> SEQUENCE: 4
atgacggaca tcaaggccac atcaagtaca tcggccacta cagcaccaac agcaggccga     60
ccagcgcgtc gacttggaca aatttccctc gtcgcctgtc tcggcggact tctcttcggc    120
tatgacaccg gtgtcgccaa cggcgccgaa ggccacatgg cacaagaact cggactcaac    180
gtgctgcagc tcggcgttgt catcagttca ctggttttcg ctgcagcctt tggcgcgctg    240
ttcgctgggc gtatctcgga cgaaatcggg cgtcgaaaag caattatcac tttgtccgtg    300
ctgttcttcc tcggatcaat cctcgtcgta ttctcccccg ccggtgagct ggggcagttc    360 tacgaccag gatttgccac cttggtcacc gggcgcatca tgtttgggtct cgcggttggc    420 ggcgcctcca cagtagttcc ggtgtacctc gctgaactcg caccactaga aatccgcggc    480
tccctgaccg gccgaaacga gcttgctatc gtcaccggcc agctgcttgc cttcgtgatc    540
aacgcgctta tcgccgtcac cctacacgga gttattgatg gaatctggcg catcatgttc    600
gccgtctgtg ccctccctgc cgtcgccctc ttcctcggca tgctgcggat gccggaatca    660
ccacgctggc tggtcaacca ggggcgttac gacgacgccc gccgcgtcat ggagaccgtc    720 cgtaccctg agcgtgcgaa agccgaaatg gatgaaatca tcgcggtgca ctctgaaaac    780
aatgcggcac ttcctggtgt taagcagtct tcgggccagg cttcaggcca ggtttctagc    840
aagcacaccc acatgtccat cggcgaagtc ctcagcaaca aatggctggt tcgtctgctc    900
atcgccggca tcggtgttgc agttgcccag cagctcaccg gcatcaacgc catcatgtac    960 tacgaaccc gcgtcctcga ggaatccggc atgagcgcag aaatggctgt ggttgccaac    1020
attgctttcg gtgccgttgc cgtcatcggt ggactgatcg cactgcgcaa catggaccgc    1080
ctggatcgcc gcaccacctt catcatcggc ctgtcactga ccaccacctt ccacttttg    1140 atcgcagctg ccggcactct ccttccagaa ggtaactcca ttcgaccatt cgccatcatg    1200
atccttgttg ttgggttcgt gctctccatg cagactttcc tcaacgttgc agtgtgggtg    1260
tggctggcgg aaatcttccc agtccgaatg aagggtatcg gcaccggtat ttcggtattc    1320
tgcggttggg gcatcaatgg cgtcctagcg ttgttcttcc cagcactggt ctccggcgtg    1380
ggtatcacct tctccttcct tatcttcgca gtcgtcggag tcattgccct ggcgttcgtc    1440
accaagtttg ttcctgaaac ccgtggccgc tcacttgaag aactcgatca cgcagcattc    1500
accggccaga tcttcaagaa ggcttaa                                        1527

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5
tagcaagctt actgaccccg accgctgta                                       29
```

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
tagcaagctt ggtgatttgg aatccaaac                              29

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
gatcgaattc tggtttgcat atttgatc                               28

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
gatcgaattc tgtgggaggg tgtcg                                  25

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
taactaagct tataaatgtt agtgtaagc                              29

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aagaggtggc ttcctccgcg                                        20

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
ggatgtgctg caaggcgatt aagttgg                                27

<210> SEQ ID NO 12
<211> LENGTH: 26
<212> TYPE: DNA
<213> ORGANISM: Artificial Sequence
<220> FEATURE:

```
<223> OTHER INFORMATION: primer

<400> SEQUENCE: 12
ctcgtatgtt gtgtggaatt gtgagc                                          26

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
cgggcctctt cgctattacg c                                               21

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
aggcttaccc gtcttactgt c                                               21
```

RECOMBINANT MICROORGANISMS OF *ESCHERICHIA* WITH L-THREONINE PRODUCTIVITY AND METHOD OF PRODUCING L-THREONINE USING THE SAME

CROSS REFERENCE TO RELATED APPLICATIONS

This application is a National Stage Entry of International Application No. PCT/KR2014/003649 filed on Apr. 25, 2014, and claims the benefit of International Application No. PCT/KR2014/001154, filed on Feb. 12, 2014, which is hereby incorporated by reference in its entirety for all purposes as if fully set forth herein.

TECHNICAL FIELD

The present invention relates to a recombinant microorganism of the genus *Escherichia* having enhanced L-threonine productivity, which is obtained by modifying a microorganism of the genus *Escherichia* so as to express the permease of *Corynebacterium* origin, and to a method of producing L-threonine using the recombinant microorganism.

Incorporated by reference herein in its entirety is the Sequence Listing entitled "Sequence list.txt", created Jul. 12, 2016 size of 15 kilobytes.

BACKGROUND ART

L-threonine, a kind of essential amino acid, is widely used as an additive to animal feed and food, and as fluids and synthetic materials for medical and pharmaceutical use. L-threonine is mainly produced by fermentation using *Escherichia coli, Serratia, Providencia* or *Corynebacterium*, developed by artificial mutation methods or gene recombination methods, or artificial mutant strains thereof. Genes related to the biosynthesis of threonine and various methods for increasing the expression of these genes have been developed, but the demand for a method capable of producing L-threonine in high yield in a more cost-effective manner still exists.

It is known that GalP protein that is encoded by galP in *E. coli* is galactose permease that transports a variety of monosaccharides, including galactose and glucose, into cells (V. Hernandez-Montalvo F. Valle F. Bolivar G. Gosset, Appl Microbiol Biotechnol (2001) 57:186-191). In addition, it is known that the GalP protein also acts as glucose permease (Venter, Henrietta et al., Biochemical Journal (2002) 363: 243-252). It was reported that, when the expression of the galP gene in *E. coli* is increased, for example, by increasing the copy number of the gene, the production of threonine in the *E. coli* is increased (WO 2004/087937).

It was reported that inositol permease that is encoded by iolT1 and iolT2 genes in *Corynebacterium glutamicum* can also act as glucose permease (Ikeda et al., Appl Microbial Biotechnol (2011) 90:1443-1451). It was also reported that iolT1 and iolT2 genes have high homology with the galP gene of *E. coli*. However, the correlation between inositol permease and threonine production has not yet been reported.

The present inventors have found that, when iolT1 gene and/or iolT2 gene encoding inositol permease in microorganisms of the genus *Corynebacterium* is introduced into a microorganism of the *Escherichia Coli*, the microorganism of the genus *Escherichia* has enhanced L-threonine productivity, thereby completing the present invention.

DISCLOSURE

Technical Problem

Therefore, it is an object of the present invention to provide a recombinant microorganism of the genus *Escherichia* having enhanced L-threonine productivity, which is obtained by modifying a microorganism of the *Escherichia* so as to express the permease of *Corynebacterium* origin.

Another object of the present invention is to provide a method of producing L-threonine in high yield using the recombinant microorganism.

Technical Solution

In order to accomplish the above object, the present invention provides a recombinant microorganism of the genus *Escherichia*, obtained by transforming a microorganism of the genus *Escherichia* so as to express the permease of *Corynebacterium glutamicum* origin.

The present invention also provides a method of producing L-threonine in high yield using the recombinant microorganism.

Advantageous Effects

According to the present invention, the growth rate of a strain is greatly increased compared to those of conventional strains so that the strain can produce L-threonine in high yield. Thus, the production of industrially significant L-threonine can be greatly increased.

DESCRIPTION OF DRAWINGS

FIG. 1 shows the homology alignment of the amino acid sequences of the galP of *E. coli* origin and the iolT1 and iolT2 of *Corynebacterium glutamicum* origin.

FIG. 2 shows a cleavage map of the recombinant vector pCC1BAC-iolT1 comprising the iolT1 gene of *Corynebacterium glutamicum* origin.

FIG. 3 shows a cleavage map of the recombinant vector pCC1BAC-iolT2 comprising the iolT2 gene of *Corynebacterium glutamicum* origin.

FIG. 4 shows a cleavage nap of the recombinant vector pCC1BAC-iolT1-iolT2 comprising the iolT1 and iolT2 genes of *Corynebacterium glutamicum* origin.

MODE FOR INVENTION

The present invention provides a recombinant microorganism of genus *Escherichia* having enhanced L-threonine productivity, which is obtained by transforming a microorganism, of the genus *Escherichia* so as to express the permease of *Corynebacterium* origin.

In the present invention, the permease of *Corynebacterium* origin may be of *Corynebacterium glutamicum* origin, and preferably *Corynebacterium glutamicum* ATCC 13032 origin, but is not limited thereto.

Most preferably, the permease of *Corynebacterium* origin may have an amino acid sequence represented by SEQ ID NO: 1 or SEQ ID NO: 2. The permease of *Corynebacterium* origin having the amino acid sequence of SEQ ID NO: 1 is encoded by the iolT1 gene having a nucleotide sequence represented by SEQ ID NO: 3, and the permease of *Coryne-*

*bacterium* origin having the amino acid sequence of SEQ ID NO: 2 is encoded by the iolT2 gene having a nucleotide sequence represented by SEQ ID NO: 4.

In addition, mutants having a mutation in the amino acid sequences of the above proteins, or permeases having a homology of at least 80%, preferably at least 90%, more preferably at least 95%, and particularly preferably at least 97%, to the amino acid sequences of the above proteins, are also included in the scope of the present invention, as long as they are proteins having permease activity as disclosed in the present invention.

As used herein, the term "homology" refers to the identity between two amino acid sequences. The homology can be determined using methods well known to those skilled in the art, for example, BLAST 2.0 which calculates parameters such as score, identity or similarity.

Figure 1:
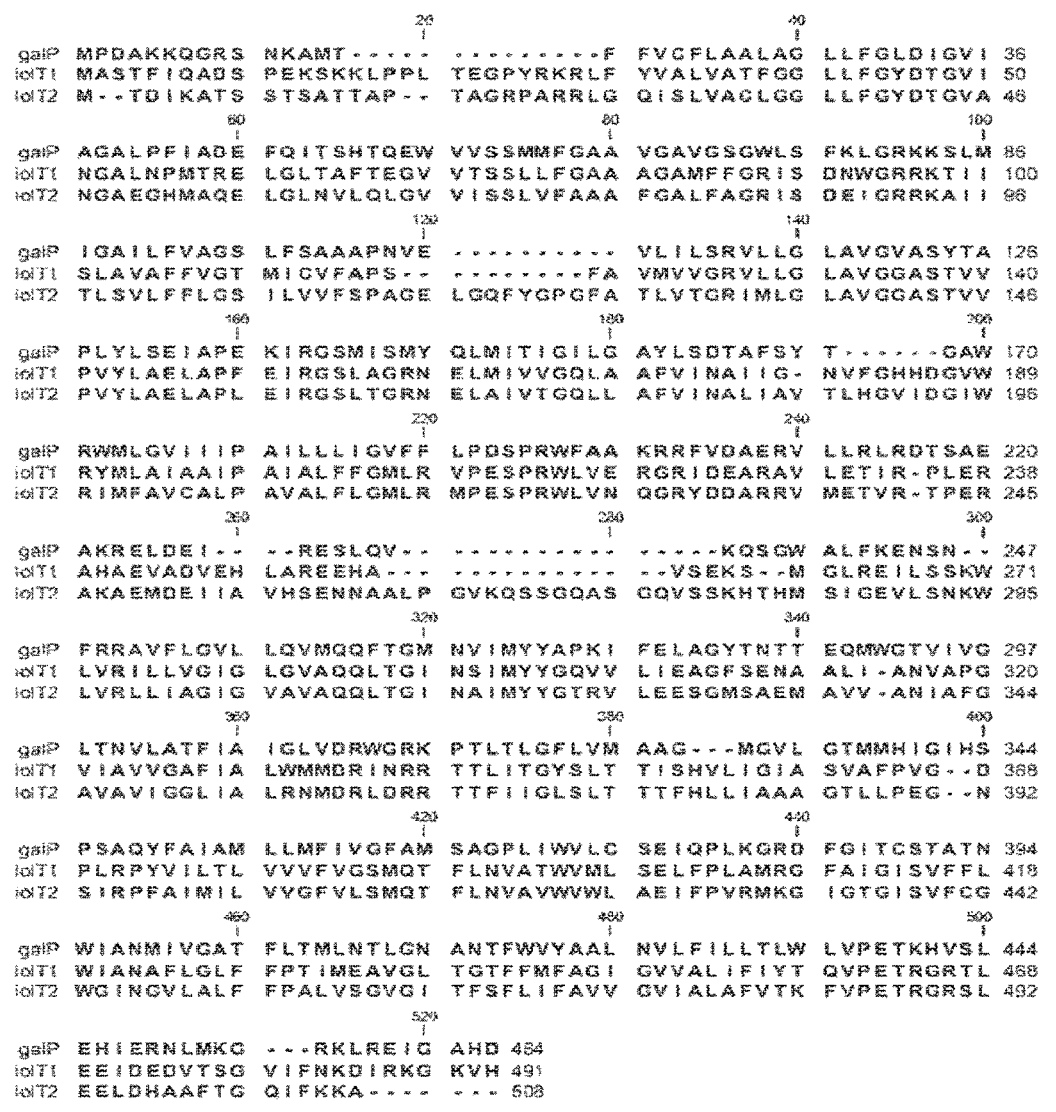

In an example of the present invention, genes having homology to the galP gene that encodes glucose permease in *E. coli* were identified from *Corynebacterium glutamicum* ATCC 13032. As a result, the amino acid sequence encoded by iolT1 (NCBI Reference Sequence: NC_006958.1, cg0223) derived from *Corynebacterium glutamicum* ATCC 13032 showed a homology of 34% to the amino acid sequence of *E. coli* galP, and the amino acid sequence encoded by iolT2 (NCBI Reference Sequence: NC_006958.1, cg3387) showed a homology of 31% to the amino acid sequence of the *E. coli* galP (see FIG. 1).

The *E. coli* galP is known, and can be obtained from the *E. coli* genome sequence (Accession no. AAC75876) described in Blattner et al., Science 277: 1453-1462 (1997), and can also be obtained from databases such as the National Center for Biotechnology Information (NCBI) database and the DNA Databank of Japan (DDBJ) database.

The microorganism of the genus *Escherichia* having L-threonine productivity according to the present invention may be *E. coli* or an L-threonine-producing *E. coli* mutant. More preferably, the microorganism of the genus *Escherichia* having L-threonine productivity is *E. coli* KCCM 10541 (Korean Patent No. 10-0576342) derived from *E. coli* KFCC 10718 (Korean Patent No. 10-0058286). *E. coli* KCCM 10541 is an L-threonine-producing strain that has a methionine auxotroph phenotype, resistance to a threonine analogue, resistance to a lysine analogue, resistance to an isoleucine analogue, and resistance to a methionine analogue, and comprises two or more copies of phosphoenol pyruvate carboxylase gene (ppc gene) and threonine operon introduced into the chromosome.

A method that enables the permease-encoding gene to be expressed in the microorganism of the genus *Escherichia* having L-threonine productivity according to the present invention is not specifically limited. For example, in order to enable the expression of the permease-encoding gene, a recombinant vector comprising the permease-encoding gene may be transformed into a microorganism, or the copy number of the permease-encoding gene may be increased, or an expression regulatory sequence of the permease-encoding gene may be modified. In addition, two or more of these methods may also be used in combination. Generally, methods for increasing the expression level of the related to threonine biosynthesis-related gene include a method of increasing the copy number of the gene in a single microorganism. For this, a plasmid whose copy number is maintained at a high level is used (Sambrook et al., Molecular cloning, $2^{nd}$ edition, 1989, 1.3-1.5). Specifically, a desired gene is inserted into a plasmid whose copy number is maintained at a high level, and the resulting recombinant plasmid is transformed into a microorganism. In this case, the effect of increasing the copy number of the gene to the copy number of the plasmid per microorganism can be obtained. In addition, a method of inserting the threonine biosynthesis-related gene into chromosomal DNA may also be used.

In one embodiment, the present invention provides a recombinant vector comprising the iolT1 gene and/or iolT2 gene of *Corynebacterium glutamicum* origin, and a recombinant microorganism of the genus *Escherichia* having enhanced L-threonine productivity, which is obtained by transformation with the recombinant vector.

As used herein, the term "vector" refers to a DNA construct containing the nucleotide sequence of a target protein-encoding gene operably linked to a suitable regulatory sequence so as to be able to express the target gene in a suitable host cell. The regulatory sequence includes a promoter capable of initiating transcription, any operator for regulating this transcription, a sequence encoding a suitable mRNA ribosome binding site, and a sequence for regulating the termination of transcription and translation. Once transformed into a suitable host, the vector may replicate or function independently of the host genome, or may integrate into the genome itself.

The vector that is used in the present invention is not specifically limited and may be any vector known in the art, as long as it can replicate in a host. Examples of the commonly used vectors may include natural or recombinant plasmids, cosmids, viruses, and bacteriophages.

The present invention provides a recombinant vector comprising the join gene of *Corynebacterium glutamicum* origin. Preferably, the recombinant is pCC1BAC-iolT1. More preferably, the recombinant vector has a cleavage map shown in FIG. 2.

The present invention also provides a recombinant vector comprising the iolT2 gene of *Corynebacterium glutamicum* origin. Preferably, the recombinant vector is pCC1BAC-iolT2. More preferably, the recombinant vector has a cleavage map shown in FIG. 3.

The present invention also provides a recombinant vector for simultaneously expressing the iolT1 and iolT2 genes of *Corynebacterium glutamicum* origin. Preferably, the recombinant vector is pCC1BAC-iolT1-iolT2. More preferably, the recombinant vector has a cleavage map shown in FIG. 4.

As used herein, the term "transformation" means introducing a vector comprising a polynucleotide encoding a target protein into a host cell so as to be able to express a protein encoded by the polynucleotide in the host cell. The transformed polynucleotides include all the genes inserted in the chromosome or the host cell or located, outside the chromosome, as long as they can be expressed in the host cell. In addition, the polynucleotides include DNA and RNA, which encode the target protein. As long as the polynucleotide can be introduced in the host cell and expressed therein, the gene may be introduced in any form. For example, the polynucleotide can be introduced into the host cell in the form of an expression cassette which is a polynucleotide construct including all elements for expressing the gene. The expression cassette includes a promoter which is operably linked to the gene, a transcription termination signal, a ribosome binding site, and a translation termination signal. The expression cassette may be in the form of an expression vector capable of self-replicating. The polynucleotide may also be introduced into the host cell by itself, and be operably linked to the sequence necessary for expression in the host cell.

In one aspect, the present invention provides a microorganism of the genus *Escherichia* having enhanced L-threonine productivity, wherein the microorganism is obtained by transformation with a recombinant vector comprising the iolT1 gene or iolT2 gene of *Corynebacterium glutamicum* origin.

In another aspect, the present invention provides a microorganism of the genus *Escherichia* having enhanced L-threonine productivity, wherein the microorganism is obtained by transformation with a recombinant vector comprising the iolT1 gene and iolT2 gene of *Corynebacterium glutamicum* origin.

Preferably, the transformed recombinant microorganism of the genus *Escherichia* may be *E. coli*. More preferably, the microorganism may be *E. coli* CA03-0230 (KCCM11370P), *E. coli* CA03-0260 (KCCM11369P) or *E. coli* CA03-0231 (KCCM11371P).

The recombinant, threonine-producing strains of the present invention, as described above, comprises the join and/or iolT2 gene of *Corynebacterium* origin introduced into *E. coli*, in which the introduced gene can increase the expression of permease in the *E. coli* strain to thereby greatly increase the sugar consumption rate and growth rate of the strain. Thus, the strains of the present invention can produce L-threonine at high concentration.

The present invention also provides a method for producing L-threonine, the method comprising the steps of: culturing the transformed recombinant microorganism of the genus *Escherichia*; and separating L-threonine from the culture of the microorganism.

The recombinant microorganism of the genus *Escherichia* according to the present invention can be cultured by any conventional method. Specifically, the microorganism can be cultured by inoculating it into a medium that totally or partially contains sucrose or glucose as a carbon source. The culture process can be performed in suitable media and culture conditions known in the art. This culture process can be easily modified by any person skilled in the art depending on the type of strain selected. Examples of the culture process include, but are not limited to, batch culture, continuous culture, and fed-batch culture. The medium that is used in culture of the microorganism of the present invention should properly satisfy the requirements of the microorganism of the present invention.

Specifically, the medium that is used in the present invention contains sucrose or glucose as a main carbon source. Further, molasses containing a high concentration of sucrose may also be used as a carbon source. In addition, suitable amounts of various carbon sources may be used. Preferably, purified glucose is used. Examples of nitrogen sources that may be used in the present invention include organic nitrogen sources such as peptone, yeast extract, meat extract, malt extract, corn steep liquor, and soy meal, and inorganic nitrogen sources such as urea, ammonium sulfate, ammonium chloride, ammonium phosphate, ammonium carbonate, and ammonium nitrate. Preferably, peptone is used. These nitrogen sources may be used alone or in combination. The medium may contain potassium phosphate monobasic, potassium phosphate dibasic and corresponding sodium-containing salts, as phosphorus sources. Further, the medium may contain a metal salt such as magnesium sulfate or iron sulfate. In addition, the medium may contain amino acids, vitamins and suitable precursors. These media or precursors may be added to the medium in a batch or continuous manner.

The culture medium is typically maintained at a temperature ranging from 27° C. to 37° C., and preferably from 30° C. to 37° C. Culture of the microorganism can be continued until the desired level of the useful substance will be obtained. Preferably the culture period is from 10 to 100 hours.

Hereinafter, the present invention will be described in further detail with reference to examples. It is to be understood, however, that these examples are for illustrative purposes only and are not intended to limit the scope of the present invention.

EXAMPLES

Comparative Example: Construction of Recombinant Strains by Transformation with Recombinant Vector Comprising *E. coli* galP Gene and Comparison of L-Threonine Productivity It was reported that galactose permease in *E. coli* functions as glucose permease, and when the expression of galactose permease is increased, for example, by increasing the copy number of galactose permease, the threonine productivity of the *E. coli* strain is increased (WO 2004/087937). To verify this report, a recombinant strain was constructed by increasing the copy number of the galP gene in the L-threonine-producing strain KCCM 10541, and the L-threonine productivity thereof was evaluated.

(1) Construction of Recombinant Vector Comprising *E. coli*, galP Gene

To obtain a 1.4-kb fragment comprising the open reading frame of the *E. coli* galP gene, the genomic DNA of the wild-type *E. coli* strain W3110 was extracted using a Genomic-tip system (Qiagen).

A polymerase chain reaction (hereinafter abbreviated as "PCR") was performed using the genomic DNA (gDNA) as a template. The PCR reaction was performed using primers of SEQ ID NOS: 9 and 10 under the following conditions: 30 cycles, each consisting of denaturation at 94° C. for 30 sec, annealing at 56° C. for 30 sec, and elongation at 72° C. for 50 sec. The PCR product (hereinafter referred to as "galP fragment") was electrophoresed on 0.8% agarose gel, and then a band having a desired size was eluted.

The obtained galP fragment was treated with the restriction enzyme HindIII, and then ligated with a linear pCC1BAC vector (EPICENTRE, hereinafter the same) treated with the same restriction enzyme HindIII so that it would be in the same orientation with the lac promoter of the vector.

*E. coli* DH5α cells were transformed with the constructed vector, and then plated on a chloramphenicol-containing LB solid medium and cultured overnight at 37° C. One platinum loop of the cultured colony was inoculated into 3 ml of a chloramphenicol-containing LB liquid medium and cultured overnight, and then plasmid DNA was recovered using a plasmid miniprep kit (QIAGEN, hereinafter the same). The size of the recombinant vector was determined by treatment with the restriction enzyme HindIII (data not shown), and the clone was identified by performing PCR using primers of SEQ ID NOS: 11 and 12 under the following conditions: denaturation at 94° C. for 30 sec, annealing at 56° C. for 30 sec, and elongation at 72° C. for 60 sec. The recombinant vector was named CC1BAC-galP (data not shown).

In addition, the galP fragment was ligated with a linear pCL1920 vector treated with the same restriction enzyme HindIII so that it would be in the same orientation as the lac promoter of the vector. *E. coli* DH5α cells were transformed with the constructed vector, and then plated on a spectinomycin-containing LB medium, and cultured overnight at 37° C. One platinum, loop of the cultured colony was inoculated into 3 ml of a spectinomycin-containing LB liquid medium and cultured overnight, and then plasmid DNA was recovered using a plasmid miniprep kit. The size of the recombinant vector was determined by treatment with the restriction enzyme HindIII (data not shown), and the clone was identified by performing PCR using primers of SEQ ID NOS: 13 and 14 under the following conditions: denaturation at 94° C. for 30 sec, annealing at 56° C. for 30 sec, and elongation at 72° C. for 60 sec. The recombinant vector was named pCL1920-galP (data not shown).

(2) Construction of Recombinant Strain by Transformation with Recombinant Vector The recombinant vector pCC1BAC-galP was introduced into the L-threonine-producing strain *E. coli* KCCM10541 as a parent strain by electroporation, and the *E. coli* strain was plated on a solid medium containing 15 µg/ml of chloramphenicol to select a single colony. In the same manner as above, the recombinant vector pCL1920-galP was introduced into the L-threonine-producing strain *E. coli* KCCM10541 by electroporation, and the *E. coli* strain was plated on a solid medium containing 50 µg/ml of spectinomycin to select a single colony.

The selected strains were named KCCM10541/pCC1BAC-galP and KCCM10541/pCL1920-galP, respectively.

(3) Comparison of L-Threonine Productivity Between Recombinant Strains

The recombinant strains constructed in the above section (2) were cultured using the threonine titer medium shown in Table 1 below in an Erlenmeyer flask according to the method described below, and the L-threonine productivites of the recombinant strains were examined.

TABLE 1

| Composition | Concentration (per liter) |
| --- | --- |
| Glucose | 70 g |
| KH$_2$PO$_4$ | 2 g |
| (NH$_4$)$_2$SO$_4$ | 27.5 g |
| MgSO$_4$•H$_2$O | 1 g |
| FeSO$_4$•H$_2$O | 5 mg |
| MnSO$_4$•H$_2$O | 5 mg |
| DL-methionine | 0.15 g |
| Yeast extract | 2 g |
| Calcium carbonate | 30 g |
| pH | 6.8 |

Titer evaluation was performed using the parent strain *E. coli* KCCM10541 and the KCCM10541/pCC1BAC-galP and KCCM10541/pCL1920-galP strains. When introduced into each of the strains, the recombinant vector pCC1BAC-galP is expressed as 1 copy, and the recombinant vector pCL1920-galP is expressed as 5 copies. The effect of the increase in the copy number was examined.

Each of the recombinant strains having different genetic characters was cultured overnight on LB solid medium in an incubator at 33° C., after which one platinum loop of each of the recombinant strains was inoculated into 25 ml of a glucose-containing titer medium having the composition shown in Table 1 above, and then was cultured in an incubator at 33° C. and 200 rpm, for 48 hours. The results of the culture are shown in Table 2 below.

TABLE 2

| Strain | L-threonine (g/L) | Sugar consumption rate (g/L/hr) |
| --- | --- | --- |
| KCCM10541 | 32.0 | 0.753 |
| KCCM10541/pCC1BAC-galP | 31.1 | 0.793 |
| KCCM10541/pCL1920-galP | 30.8 | 0.816 |

As a result, as can be seen in Table 2 above, the parent strain *E. coli* KCCM10541 produced 32.0 g/L of L-threonine when cultured for 48 hours, but the recombinant strain *E. coli* KCCM10541/pCC1BAC-galP constructed in the Comparative Example produced 31.1 g/L of L-threonine, and the recombinant strain KCCM10541/pCL1920-galP produced 30.8 g/L of L-threonine. Thus, the L-threonine productivities of these recombinant strains were reduced by 0.9 g/L and 1.2 g/L, respectively, compared to that of the parent strain.

As can be seen in Table 2 above, the parent strain *E. coli* KCCM10541 showed a sugar consumption rate of 0.753 g/L/hr, but KCCM10541/pCC1BAC-galP showed a sugar consumption rate of 0.793 g/L/hr, and KCCM 10541/pCL1920-galP showed a sugar consumption rate of 0.816 g/L/hr. The sugar consumption rates of these recombinant strains increased by 5.3% and 8.4%, respectively, compared to that of the parent strain.

Example 1: Construction of Recombinant Vector Comprising iolT1 and/or iolT2 of *Corynebacterium* Origin (1) Comparison of Homology with *E. coli* Glucose Permease (galP)

It was reported that the iolT1 and iolT2 genes encoding inositol permease in *Corynebacterium glutamicum* has homology to the galP gene encoding *E. coli* glucose permease. Genes having homology to the *E. coli* galP gene were identified from the genome of wild-type *Corynebacterium glutamicum* ATCC 13032 and compared, and the results of the comparison are shown in FIG. 1. The amino acid sequence encoded by *Corynebacterium glutamicum* iolT1 showed a homology of 34% to the amino acid sequence encoded by *E. coli* galP, and the sequence encoded by *Corynebacterium glutamicum* iolT2 showed a homology of 31% to the amino acid sequence encoded by *E. coli* galP.

(2) Preparation of iolT1 Gene Fragment

To obtain a 1.5-kb fragment comprising the open reading frame of the iolT1 gene of SEQ ID NO: 3, the genomic DNA of *Corynebacterium glutamicum* ATCC 13032 was extracted using Genomic-tip system (Qiagen).

A polymerase chain reaction was performed using the genomic DNA (gDNA) as a template. The PCR reaction was performed using primers of SEQ ID NOS: 5 and 6 under the following conditions: 30 cycles, each consisting of denaturation at 94° C. for 30 sec, annealing at 56° C. for 30 sec, and elongation at 72° C. for 60 sec. The PCR product (hereinafter referred to as "iolT1 fragment") was electrophoresed on 0.8% agarose gel, and then a band having a desired size was eluted.

(3) Construction of Recombinant Vector pCC1BAC-iolT1

The iolT1 fragment prepared in Example 1-(2) above was treated with the restriction enzyme HindIII, and then ligated with a linear pCC1BAC vector treated with the same restriction enzyme HindIII so that it would be in the same orientation with the lac promoter of the vector.

*E. coli* DH5α cells were transformed with the constructed vector, and then plated on a chloramphenicol-containing LB solid medium and cultured overnight at 37° C. One platinum loop or the cultured colony was inoculated into 3 ml of a chloramphenicol-containing LB liquid medium and cultured overnight, and then plasmid DNA was recovered using a plasmid miniprep kit. The size of the recombinant vector was determined by treatment with the restriction enzyme HindIII (data not shown), and the clone was identified by performing PCR using primers of SEQ ID NOS: 11 and 12 under the following conditions: denaturation at 94° C. for 30 sec, annealing at 56° C. for 30 sec, and elongation at 72° C. for 90 sec. The recombinant vector was named pCC1BAC-iolT1.

(4) Preparation of iolT2 Gene Fragment

To obtain a 1.6-kb fragment comprising the open reading frame of the iolT2 gene of SEQ ID NO: 4, the genomic DNA of *Corynebacterium glutamicum* ATCC 13032 was extracted using a Genomic-tip system (Qiagen).

A polymerase chain reaction was performed using the genomic DNA (gDNA) as a template. The PCR reaction was performed using primers of SEQ ID NOS: 7 and 8 under the following conditions: 30 cycles, each consisting of denaturation at 94° C. for 30 sec, annealing at 56° C. for 30 sec, and elongation at 72° C. for 60 sec. The PCR product (hereinafter referred to as "iolT2 fragment") was electrophoresed on 0.8% agarose gel, and then a band having a desired size was eluted.

(5) Construction of Recombinant Vector pCC1BAC-iolT2

The iolT2 fragment prepared in Example 1-(4) above was treated with the restriction enzyme EcoRI, and then ligated with a linear pCC1BAC vector treated with the same restriction enzyme EcoRI so that it would be in the same orientation with the lac promoter of the vector.

*E. coli* DH5a cells were transformed with the constructed vector, and then plated on a chloramphenicol-containing LB solid medium and cultured overnight at 37° C. One platinum loop of the cultured colony was inoculated into 3 ml of a chloramphenicol-containing LB liquid medium and cultured overnight, and then plasmid DNA was recovered using a plasmid miniprep kit. The size of the recombinant vector was determined by treatment with the restriction enzyme EcoRI (data not shown), and the clone was identified by performing PCR using primers of SEQ ID NOS: 11 and 12 under the following conditions: denaturation at 94° C. for 30 sec, annealing at 56° C. for 30 sec, and elongation at 72° C. for 90 sec. The recombinant vector was named pCC1BAC-iolT2.

(6) Construction of Recombinant Vector pCC1BAC-iolT1-iolT2

The pCC1BAC-iolT2 vector constructed in Example 1-(5) above was treated with the restriction enzyme HindIII, and then ligated with the iolT1 fragment prepared in Example 1-(2) above so that so that it would be in the same orientation with the lac promoter of the vector.

*E. coli* DH5a cells were transformed with the constructed vector, and then plated on a chloramphenicol-containing LB solid medium, and cultured overnight at 37° C. One platinum loop of the cultured colony was inoculated into 3 ml of a chloramphenicol-containing LB liquid medium and cultured overnight, and then plasmid DNA was recovered using a plasmid miniprep kit. The size of the recombinant vector was determined by treatment with the restriction enzyme HindIII (data not shown), and the clone was identified by performing PCR using primers of SEQ ID NOS: 11 and 12 under the following conditions: denaturation at 94° C. for 30 sec, annealing at 56° C. for 30 sec, and elongation at 72° C. for 120 sec. The recombinant vector was named pCC1BAC-iolT1-iolT2.

Example 2: Construction of Recombinant Strains by Transformation and Comparison of L-Threonine Productivity (1) Construction of Recombinant Strains Using Wild-Type *E. coli*

Each of the recombinant vectors (pCC1BAC-iolT1, pCC1BAC-iolT2 and pCC1BAC-iolT1-iolT2) constructed in Example 1 above was introduced into wild-type *E. coli* MG1655 comprising the threonine operon-overexpressing vector pRRThrABCR3 (Lee K H et al., Molecular Systems Biology (2007) 3:149) by electroporation, and then the *E. coli* cells were plated on solid media containing 100 μg/ml of ampicillin and 15 μg/ml of chloramphenicol to select single colonies.

The selected strains were named MG1655/pBRThrABCR3/pCC1BAC-iolT1, MG1655/pBRThrABCR3/pCC1BAC-iolT2 and MG1655/pBRThrABCR3/pCC1BACiolT1-iolT2, respectively.

The L-threonine productivities of these strains were analyzed in the same manner as described in Comparative Example 1-(3) above using the threonine titer medium having the composition shown in Table 1 above, and the results of the analysis are shown in Table 3 below.

TABLE 3

| Strain | L-threonine (g/L) | Sugar consumption rate (g/L/hr) |
|---|---|---|
| MG1655/pBRThrABCR3 | 3.86 | 0.877 |
| MG1655/pBRThrABCR3/pCC1BAC-iolT1 | 3.88 | 1.109 |
| MG1655/pBRThrABCR3/pCC1BAC-iolT2 | 3.92 | 1.035 |
| MG1655/pBRThrABCR3/pCC1BAC-iolT1-iolT2 | 3.85 | 1.123 |

As a result, as can be seen in Table 3 above, the parent strain *E. coli* MG1655 produced 3.86 g/L of L-threonine when cultured for 48 hours, and the recombinant strain MG1655/pCC1BAC-iolT1 constructed in the Example of the present invention produced 3.88 g/L of L-threonine, and the recombinant strains MG1655/pCC1BAC-iolT2 and MG1655/pCC1BAC-iolT1-iolT2 produced 3.92 g/L and 3.85 g/L of L-threonine, respectively. In other words, the recombinant strains produced L-threonine at levels similar to that of the parent strain.

As can be seen in Table 3 above, the wild-type parent strain *E. coli* MG1655 showed a sugar consumption rate of 0.877 g/L/hr, but MG1655/pCC1BAC-iolT2, MG1655/pCC1BAC-iolT1 and MG1655/pCC1BAC-iolT1-iolT2 showed sugar consumption rates of 1.035 g/L/hr, 1.109 g/L/hr and 1.123 g/L/hr, which increased by 18.0%, 26.5% and 26.1%, respectively, compared to that of the parent strain.

(2) Construction of Recombinant Strains Using *E. coli* KCCM 10541

Each of the recombinant vectors (pCC1BAC-iolT1, pCC1BAC-iolT2 and pCC1BAC-iolT1-iolT2) constructed in Example 1 above was introduced into the L-threonine-producing strain *E. coli* KCCM10541 as a parent strain by electroporation, and then the *E. coli* cells were plated on solid media containing 15 μg/ml of chloramphenicol to select single colonies.

The selected strains were named KCCM10541/pCC1BAC-iolT1, KCCM10541/pCC1BAC-iolT2 and KCCM10541/pCC1BAC-iolT1-iolT2, respectively.

The L-threonine productivities of these strains together with the recombinant microorganisms obtained in Comparative Example 1-(2) above were analyzed in the same manner as described in Comparative Example 1-(3) using the threonine titer medium having the composition shown in Table 1 above, and the results of the analysis are shown in Table 4 below.

TABLE 4

| Strain | L-threonine (g/L) | Sugar consumption rate (g/L/hr) |
|---|---|---|
| KCCM 10541 | 30.3 | 0.823 |
| KCCM 10541/pCC1BAC-iolT1 | 29.5 | 1.213 |
| KCCM 10541/pCC1BAC-iolT2 | 32.5 | 1.093 |
| KCCM 10541/pCC1BAC-iolT1-iolT2 | 29.9 | 1.200 |
| KCCM 10541/pCC1BAC-galP | 29.8 | 0.862 |
| KCCM 10541/pCL1920-galP | 29.3 | 0.884 |

As a result, as can be seen in Table 4 above, the parent strain E. coli KCCM 10541 produced 30.3 g/L of L-threonine when cultured for 48 hours, and the recombinant strain KCCM 10541/pCC1BAC-iolT2 constructed in Example 2-(2) above showed an increase in L-threonine production by 2.2 g/L compared to the parent strain, and KCCM10541/pCC1BAC-iolT1 and KCCM10541/pCC1BAC-iolT1-iolT2 produced 29.5 g/L and 29.9 g/L of L-threonine, respectively. In other words, these recombinant strains produced L-threonine at levels similar to that of the parent strain.

The strains KCCM 10541/pCC1BAC-galP and KCCM 10541/pCL1920-galP showing an increased expression of the E. coli galP gene produced 29.8 and 29.3 g/L of L-threonine, respectively.

As can be seen in Table 4 above, the parent strain E. coli KCCM 10541 showed a sugar consumption rate of 0.823 g/L/hr, but KCCM 10541/pCC1BAC-iolT2, KCCM 10541/pCC1BAC-iolT1-iolT2 and KCCM 10541/pCC1BAC-iolT1 showed sugar consumption rates of 1.093 g/L/hr, 1.200 g/L/hr and 1.213 g/L/hr, respectively, which increased by 32.8%, 45.8% and 47.4%, respectively, compared to that of the parent strain. In addition, because the sugar consumption rates of KCCM 10541/pCC1BAC-galP and KCCM 10541/pCL1920-galP increased by 4.7% and 7.4%, respectively, compared to that of the parent strain, it can be seen that the sugar consumption rates of the strains introduced with the Corynebacterium iolT1 and/or iolT2 gene significantly increased.

The transformed E. coli strains, KCCM 10541/pCC1BAC-iolT1, KCCM 10541/pCC1BAC-iolT2 and KCCM 10541/pCC1BAC-iolT1-iolT2, were named CA03-0230, CA03-0260 and CA03-0231, respectively, and were deposited in the Korean Culture Center of Microorganisms; hereinafter abbreviated as 'KCCM') on Feb. 5, 2013 under accession numbers KCCM11370P, KCCM11369P and KCCM11371P, respectively.

The above-described results support that, when the expression of Corynebacterium permease in E. coli having L-threonine productivity is increased, that is, when one or more of the iolT1 and iolT2 genes are introduced into the E. coli strain, the sugar consumption rate increases, and the time required to produce the same concentration of L-threonine, that is, the threonine productivity increases, compared to when the expression of E. coli glucose permease in E. coli having L-threonine productivity is increased.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

ACCESSION NUMBERS

Depository authority: Korean Culture Center of Microorganisms;
Accession number: KCCM11370P;
Deposit date: Feb. 5, 2013.
Depository authority: Korean. Culture Center of Microorganisms;
Accession number: KCCM11369P;
Deposit date: Feb. 5, 2013.
Depository authority: Korean Culture Center of Microorganisms;
Accession number: KCCM11371P;
Deposit date: Feb. 5, 2013.

The invention claimed is:

1. A recombinant microorganism of the genus *Escherichia* having an enhanced rate of producing L-threonine as compared to the parent strain, wherein the recombinant microorganism is obtained by transformation so as to contain permease of *Corynebacterium* origin having SEQ ID NO: 1 or SEQ ID NO: 2.

2. The recombinant microorganism of the genus *Escherichia* according to claim 1, wherein the recombinant microorganism is *Escherichia coli*.

3. The recombinant microorganism of the genus *Escherichia* according to claim 1, wherein the recombinant microorganism is obtained by transformation so as to contain both the *Corynebacterium* permeases of SEQ ID NO: 1 and SEQ ID NO: 2.

4. A method for producing L-threonine, comprising the steps of: inoculating and culturing the microorganism of claim 1; and separating L-amino acid from the culture.

5. A method for producing L-threonine, comprising the steps of: inoculating and culturing the microorganism of claim 2; and separating L-amino acid from the culture.

6. A method for producing L-threonine, comprising the steps of: inoculating and culturing the microorganism of claim 3; and separating L-amino acid from the culture.

* * * * *